United States Patent
Bell

(10) Patent No.: US 7,625,761 B2
(45) Date of Patent: Dec. 1, 2009

(54) FLEXIBLE REACTOR

(75) Inventor: Michael L. Bell, Fullerton, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 775 days.

(21) Appl. No.: 10/903,945

(22) Filed: Jul. 30, 2004

(65) Prior Publication Data

US 2006/0024201 A1 Feb. 2, 2006

(51) Int. Cl.
*G01N 1/00* (2006.01)

(52) U.S. Cl. .................................... 436/174
(58) Field of Classification Search ............ 436/174
See application file for complete search history.

(56) References Cited

U.S. PATENT DOCUMENTS

| 4,446,864 | A | * | 5/1984 | Watson et al. ......... 128/207.14 |
| 4,637,396 | A | * | 1/1987 | Cook .................... 606/194 |
| 4,799,479 | A | * | 1/1989 | Spears ..................... 606/28 |
| 4,990,075 | A |   | 2/1991 | Wogoman ................. 422/58 |
| 5,100,382 | A | * | 3/1992 | Valtchev ............... 604/102.02 |
| 5,351,118 | A | * | 9/1994 | Spinell .................... 356/72 |
| 5,584,872 | A | * | 12/1996 | LaFontaine et al. ......... 607/116 |
| 5,609,574 | A | * | 3/1997 | Kaplan et al. ............... 604/508 |
| 5,779,673 | A | * | 7/1998 | Roth et al. .............. 604/101.03 |
| 2003/0040105 | A1 | * | 2/2003 | Sklar et al. ............... 435/287.2 |
| 2007/0054393 | A1 | * | 3/2007 | Kehlenbeck et al. ..... 435/309.1 |

FOREIGN PATENT DOCUMENTS

WO WO 02065121 A1 * 8/2002

OTHER PUBLICATIONS

Batts, John W. IV, "All About Fittings," Scivex, Upchurch Scientific Division, P.O. Box 1529, Oak Harbor, WA 98277 (2003).
U.S. Appl. No. 10/676,349, filed Sep. 30, 2003, Bell.

* cited by examiner

*Primary Examiner*—Walter D Griffin
*Assistant Examiner*—Bobby Ramdhanie
(74) *Attorney, Agent, or Firm*—Townsend and Townsend and Crew LLP

(57) ABSTRACT

A reaction vessel and a reaction system having an annular tube with an inlet, an outlet, and at least one expandable section between the inlet and the outlet. The expandable section of the annular tube has a first shape and a second expanded shape. The expandable section of the annular tube expands to from the first shape to the second expanded shape in response to a change in the physical environment of the annular tube. When the expandable section of the annular tube is in the second expanded shape, the portions of the annular tube adjoining the expandable section of the annular tube are substantially less expanded.

23 Claims, 3 Drawing Sheets

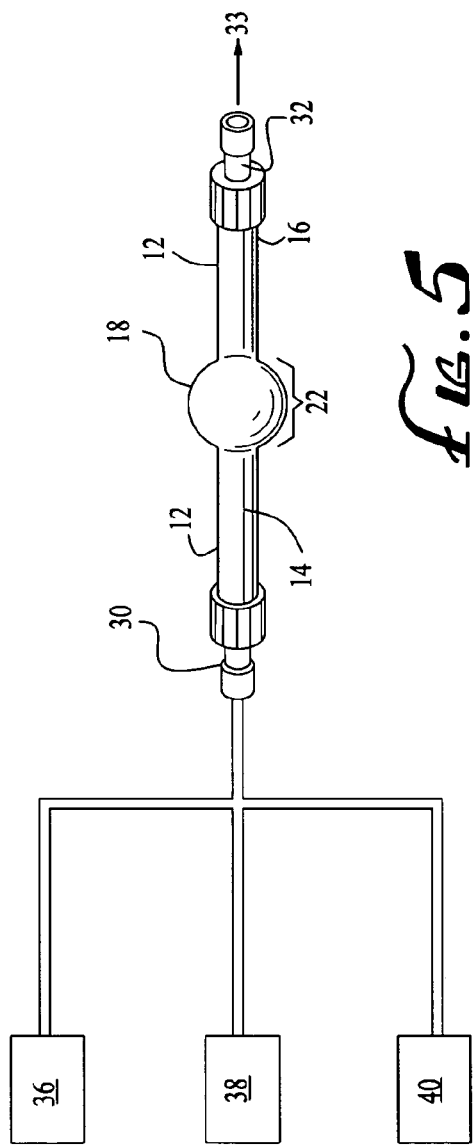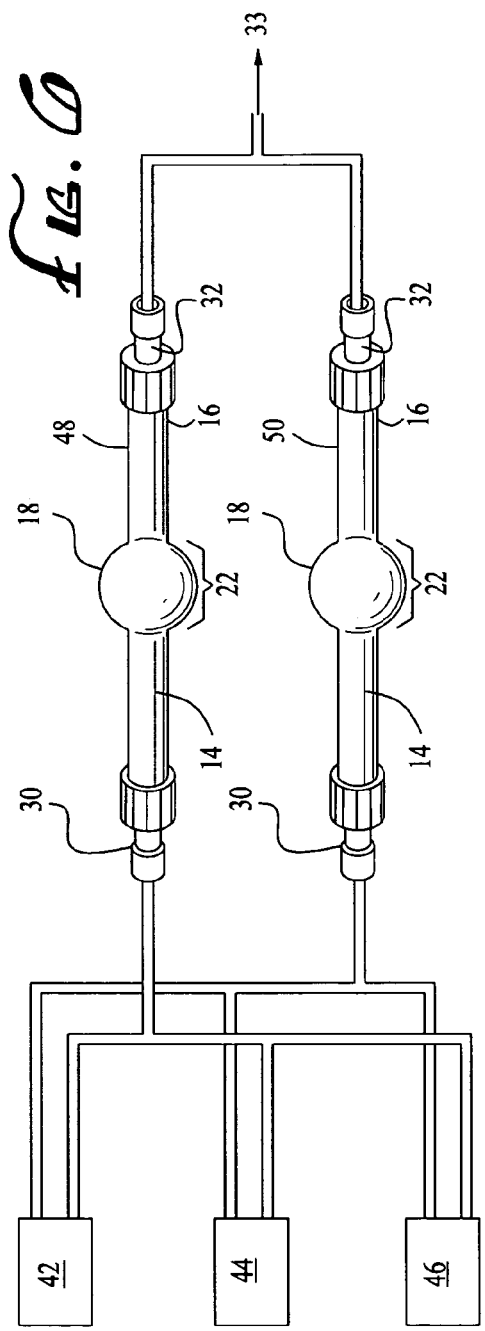

FLEXIBLE REACTOR

BACKGROUND

There is a demand for analytical systems that can be used in medical facilities having clinical laboratories such as hospitals, hospital satellite laboratories, outpatient clinics, and physician offices for performing analytical assay procedures. These medical facilities have need of cost effective methods to perform analytical tests and have need of shorter test result turnaround time to improve the quality and efficiency of patient treatment.

Various clinical analyzers used for chemical, immunochemical and biological testing of samples, such as cytometry and lateral flow immunoassays, are available for the determination of analytes. These clinical analyzers often involve a number of sequential steps in the testing procedures and can be difficult to use. Also, devices such as these can be costly and do not provide for quick removal of the liquid samples, resulting in a labor-intensive analytical procedure, and slow test result turnaround time. An example of such a known reaction vessel for detecting analytes is described in U.S. Pat. No. 4,990,075.

Therefore, there is a need for an analytical system that can be simply and efficiently operated, with high sample throughput. Such a combined system would decrease operating expenditures such as labor costs, and the cost of training employees to operate complex analyzer systems. Further, a system that can be simply operated is less likely to be subject to clinical errors and will result in higher accuracy of test results, thereby improving the quality of patient care.

SUMMARY

The present invention is directed to a flexible reactor including a reaction vessel and a reaction system. The reaction vessel and system can be used for detecting an analyte in a fluid sample, such as a biological fluid sample containing a detectable analyte.

The reaction vessel comprises an annular tube having an inlet, an outlet, and at least one expandable section between the inlet and the outlet. The expandable section has (i) a first shape when the annular tube is in a first physical environment; and (ii) a second expanded shape when the annular tube is in a second physical environment. When the expandable section of the annular tube is in the second expanded shape, the portions of the annular tube adjoining the expandable section are substantially less expanded. The annular tube is constructed (e.g., preformed) such that the expandable section of the annular tube expands to the second expanded shape in response to a change in the physical environment of the annular tube from the first physical environment to the second physical environment. Preferably, the expandable section of the annular tube changes from the first shape to the second expanded shape in response to a pressure increase inside the annular tube. Alternately, the expandable section of the annular tube can change from the first shape to the second expanded shape in response to a temperature change.

In certain preferred embodiments, the volume of the expandable section in the second expanded shape is at least twice the volume of the expandable section in the first shape, and/or the expandable section of the annular tube returns to the first shape upon return of the physical environment of the annular tube from the second physical environment to the first physical environment. In certain other preferred embodiments, the expandable section of the annular tube has a substantially uniform-diameter tubular first shape, and/or a substantially spherical second expanded shape; and/or the portions of the annular tube adjoining the expandable section of the annular tube have a substantially less expanded uniform-diameter tubular shape when the expandable section is in the second expanded shape.

The reaction vessel can additionally have a first connector for linking the annular tube inlet to a fluid source; a second connector for linking the annular tube outlet to a fluid receptacle; and/or a mixing means in the expandable section of the annular tube. Optionally, the annular tube can be elastomeric, transparent, coated, and/or colored.

In another embodiment, the invention is a system for fluid reaction and/or analysis comprising an annular tube having an inlet, an outlet, and at least one elastomeric expandable section between the inlet and the outlet. The expandable section has a first shape and a second expanded shape, with a volume greater than that of the first shape. The system also has a first fluid source for introducing a first fluid into the annular tube and reaction therein when the expandable section of the annular tube is in the second expanded shape, and a second fluid source for introducing a wash liquid, which can be an inert liquid, into the annular tube and washing the annular tube when the expandable section of the annular tube is in the first shape. The system also has a controller for controlling the introduction of the fluid and the wash liquid into the annular tube.

According to the present invention, the system can further comprise a third fluid source for introducing a third fluid into the annular tube, the third fluid containing a reactant, which can be a detector (e.g., a detectable chemical group), to react with a component of the first fluid, which can be an analyte, in the expandable section when the annular tube is in the second expanded shape. The system can also further comprise means for introducing fluid into the annular tube, means for mixing fluid in the expandable section, and means for expanding the expandable section of the annular tube. The means for expanding the expandable section of the annular tube can include closing a portion of the annular tube with a clamp or a valve, a constraining sleeve, applying varying temperatures to the expandable section, and/or varying pressure inside the annular tube. Moreover, the present invention can also contain a plurality of annular tubes in a multiplex analysis system.

The system can be used for detecting an analyte in a fluid sample, such as a biological fluid sample. According to the present invention, an analyte detection system for detecting an analyte in a fluid sample comprising an annular tube having at least one expandable section, each expandable section having a first shape and a second expanded shape is provided. The analyte detection system also has a fluid sample source, the fluid sample having a detectable analyte, and a detector fluid source, the detector fluid having a detector for the detectable analyte. The fluid sample and the detector fluid are introduced into the annular tube at sufficiently high pressure such that the expandable section of the annular tube expands into the second expanded shape and combines the fluid sample and the detector fluid in the expandable section. Also included in the analyte detection system is a wash liquid source for introducing a wash liquid (i.e., a rinse fluid) into the annular tube and washing the annular tube. The wash liquid is introduced into the annular tube when the expandable section of the annular tube is at a sufficiently low pressure such that the expandable section is substantially unexpanded. A controller for controlling the introduction of the sample fluid, detector fluid, and wash liquid into the inlet section can also be included in the analyte detection system, as well as a pump for introducing fluids into the annular tube, and various analyte detector equipment for detecting the detectable analyte.

In another embodiment according to the present invention, there is provided a method for fluid reaction and/or analysis. In one embodiment, the method comprises selecting an annular tube having at least one expandable section, each expandable section having a first shape and a second expanded shape. A first fluid is then introduced into the annular tube, followed by introducing a second fluid into the annular tube. The second fluid contains a reactant to react with a component of the first fluid in the expandable section of the annular tube when the expandable section of the annular tube is in the second expanded shape. Then, the expandable section of the annular tube is expanded into the second expanded shape and the first and second fluids are combined in the expanded section of the annular tube. Optionally, the contents of the expandable section can be combined by diffusion, or by physical mixing, and/or the combined fluids can be incubated for a time period. After the fluids are combined, all or a portion of the combined first and second fluids are displaced from the expanded section of the annular tube. A wash liquid is then introduced into the annular tube when the expandable section is in the first shape, and the annular tube is subsequently washed by flushing the wash liquid from the annular tube.

In another embodiment, the method additionally comprises displacing the first and second fluids from the annular tube. In one embodiment, a third fluid, which can be an inert material, is introduced into the annular tube. The third fluid is used to displace all or a portion of the combined first and second fluids from the expanded section of the annular tube. Alternately, in a second embodiment, the combined first and second fluids are displaced from the expanded section of the annular tube by aspirating the first and second fluids from the annular tube. Aspirating the first and second fluids from the expanded section returns the expanded section of the annular tube to the first shape.

In a preferred embodiment according to the present invention, there is provided a method for detecting an analyte in a fluid sample, such as a biological fluid sample. According to this embodiment, the method for fluid reaction and/or analysis is used, where the first fluid is a fluid sample having a detectable analyte, which is introduced into the annular tube. The second fluid is a detector fluid containing a detector for the detectable analyte, which is introducing into the annular tube. The expandable section of the annular tube is expanded into the second expanded shape at sufficiently high pressure such that the expandable section of the annular tube is expanded into the second expanded shape, thereby combining the fluid sample containing the detectable analyte and the detector fluid containing the detector in the expandable section. The detectable analyte and detector are then detected (i.e., analyzed) in situ in the annular tube, or all or a portion of the combined fluid sample and detector fluid can be displaced from the annular tube and detected (i.e., analyzed) separate from the annular tube. A wash liquid is then introduced into the annular tube when the expandable section is in the first shape, followed by flushing the wash liquid from the annular tube, which washes the annular tube, preparing the tube for subsequent fluid reaction and/or analysis.

BRIEF DESCRIPTION OF THE DRAWINGS

The features, aspects and advantages of the present invention will become better understood with regard to the following description, appended claims and accompanying figures where:

FIG. 5 is an illustration of a system having an annular tube, shown in the second expanded shape, and multiple fluid sources, according to another embodiment of the present invention; and FIG. 6 is an illustration of a multiplex analysis system having a plurality of fluid sources and a plurality of annular tubes according to another embodiment of the present invention.

DETAILED DESCRIPTION

The present invention satisfies the need for an analytical system that can be simply and efficiently operated, with high sample throughput by employing an inexpensive, flexible reaction vessel that allows operation in any orientation and permits removal of an aliquot from the vessel without air transfer. This invention can be used with a hand-held, portable diagnostic device such as that described in U.S. patent application Ser. No. 10/676,349, filed on Sep. 30, 2003, titled "Clinical Analysis System, and other devices such as cytometers. The invention can also be used as a low cost alternative to a number of existing devices such as lateral flow immunoassays.

According to the present invention, a reaction vessel and a reaction system having a section of compliant tubing that is used as a reaction chamber is provided. The reaction vessel has an annular tube with an inlet end, an outlet end, and at least one expandable section, also referred to herein as a bubble region, or a balloon bulge, between the inlet end and the outlet end of the annular tube. The ends can be connected to a pump, to fluid channels, or can be closed. Initially, prior to sample analysis or reaction, the expandable section of the annular tube is in a unexpanded first shape. The expandable section of the annular tube is expanded to a second expanded shape by a combination of a change in the ambient physical environment of the annular tube and an appropriate combination of dimensional and material properties of the tube as well. Once the reaction vessel has been expanded to the second expanded shape, the annular tube can be returned to the original unexpanded first shape and washed or rinsed for subsequent use. The tube format is advantageous in that the reaction vessel can be easily purged and washed in situ. This is especially advantageous for removing reagents with a limited shelf life because expired materials can be thoroughly removed before refilling.

The present invention is advantageous in that the reaction vessel allows for various fluids to be easily combined, mixed, and subsequently analyzed. The reaction vessel is generally small sized, requiring small sample volumes and analytical reactants for analysis. After analysis, fluids can be quickly and cleanly flushed from the reaction vessel for subsequent reuse of the reaction vessel. The present invention is further advantageous in that and the invention allows for variable reaction volumes in a single device.

Figure 1A:
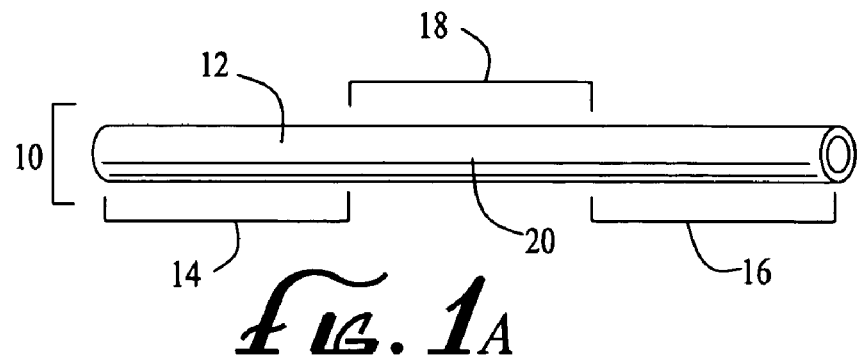
FIG. 1A is a front view of the annular tube of the present invention, shown in a first unexpanded shape.
Figure 1B:
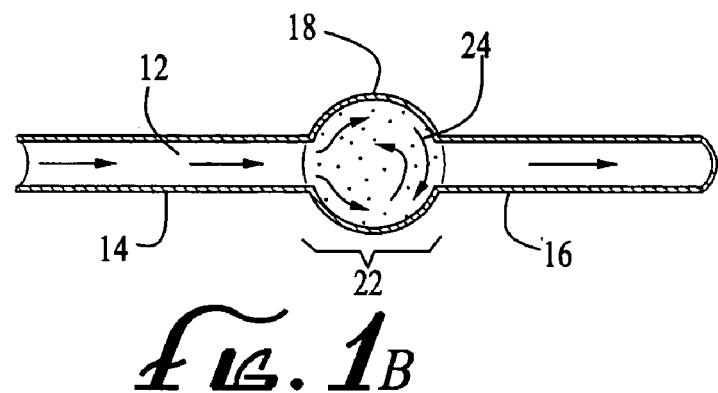
FIG. 1B is a front cross-sectional view of the annular tube of the present invention, shown in a second expanded shape.

Referring to FIGS. 1A and 1B, there is shown a reaction vessel 10 according to the present invention. As shown in FIGS. 1A and 1B, the reaction vessel has an annular tube 12 having an inlet 14 and an outlet 16, which can be interchangeable. The reaction vessel 10 also has at least one expandable section 18 between the inlet 14 and the outlet 16. FIG. 1A shows the expandable section 18 of the annular tube in an unexpanded first shape 20. FIG. 1A shows a preferred, but not required embodiment of the invention where the unexpanded first shape 20 is a substantially uniform-diameter tubular shape.

FIG. 1B shows a cross-sectional view of the expandable section 18 of the annular tube in a second expanded shape 22, which has a volume greater than that of the first shape 20. As shown in FIG. 1B, when the expandable section 18 of the annular tube is in the second expanded shape 22, the portions of the annular tube adjoining the expandable section 18 of the annular tube 12 are substantially less expanded. FIG. 1B shows a preferred, but not required embodiment of the invention where the second expanded shape 22 is a substantially spherical shape and the portions of the annular tube 12 adjoining the expandable section 18 of the annular tube 12 have a substantially less expanded uniform-diameter tubular shape. Preferably, the second expanded shape 22 is substantially expanded from that of the first shape 20. In the substantially expanded second expanded shape 22, most of the fluids can be contained (i.e., pooled) in the expandable section 18, where the fluids can be mixed or otherwise combined with other liquids or reagents, and a smaller or no portion of the fluids are contained in the portions of the annular tube 12 adjoining the expandable section 18 of the annular tube 12. In a more preferred, but not required embodiment, the volume of the expandable section 18 in the second expanded shape 22 is at least twice the volume of the expandable section 18 in the first shape 20.

The expandable section 18 of the annular tube 12 has the first shape 20 when the annular tube 12 is in a first physical environment, i.e., the internal and/or external conditions surrounding the annular tube 12 that are characterized or produced by the forces and operations of physics. Typically, the first physical environment of the annular tube 12 will be standard ambient conditions such as atmospheric pressure and room temperature. The expandable section 18 of the annular tube 12 is constructed such that the expandable section 18 has a second expanded shape when the annular tube is in a second physical environment. The expandable section 18 of the annular tube 12 expands to the second expanded shape in response to a change in the physical environment of the annular tube 12 from the first physical environment to the second physical environment. The change in the physical environment of the annular tube 12 can be a change in pressure or temperature in the interior or exterior of the annular tube, or changing the temperature of the tube itself. In a preferred, but not required embodiment, the expandable section 18 of the annular tube 12 is expanded to the second expanded shape 22 by forcing fluid under pressure into the annular tube 12. The expandable section 18 of the annular tube 12 returns to the first shape upon return of the physical environment of the annular tube 12 from the second physical environment to the first physical environment.

As shown in FIG. 1B, the reaction vessel 10 can have a mixing means 24 in the expandable section 18 of the annular tube 12. The mixing means can rely on simple diffusion within the relatively spherical expandable section 18, or the mixing means 24 can comprise active methods such as a magnetic stir bar, or agitation by sound vibration such as from a speaker attached to the expandable section 18. However, other established techniques for mixing small fluid volumes are known and can be used according to the present invention, as will be understood by those of skill in the art with reference to this disclosure.

The expandable section 18 of the annular tube 12 is expanded to the second expanded shape 22 by a combination of a change in the ambient physical environment of the annular tube 12 and an appropriate combination of dimensional and material properties of the annular tube 12 as well. For example, the expandable section 18 of the annular tube 12 can be formed from an elastomer tube and the expandable section 18 is formed by weakening a point on the elastomer tube. Alternately, an annular tube 12 with sufficient elasticity and wall thickness can be used such that the expandable section 18 propagates from a weak spot in the annular tube under pressure (i.e., a region of the annular tube having a thinner wall section will expand in response to pressure). The present invention can also be implemented using a tube with a preformed shape such as a percutaneous transluminal coronary angioplasty (PTCA) procedure balloon.

In a preferred, but not required embodiment, the expandable section 18 of the annular tube 12 is comprised of a material that is non-reactive with body fluids and reagents that may be acidic. Preferred materials are elastomers, that is, polymeric materials that have a preformed shape and can be elongated or deformed (i.e., expanded), and substantially recover from the deformation to the original preformed shape of the material. Preferred elastomers will reversibly deform by at least by a factor of two (2) without breaking or undergoing permanent deformation. Examples of preferred elastomers include silicone based polymers, natural rubber, polybutadiene-styrene, polyisoprene, nitrile based rubber (e.g., polybutadiene-acrylonitrile), butyl rubber (e.g., isobutylene-isoprene copolymer) polybutadiene, polysulfide (e.g., Hypalon™ chlorosulfonated polyethylene), polyurethane, polychloroprene (e.g., neoprene), hypalon, propylene oxide, polyacrylate, polypropylene, and flurocarbon elastomers (e.g., polytetrafluoroethylene). However, elastomers other than those listed above can be used to form the expandable section 18 of the annular tube 12, taking into consideration factors such as chemical resistance and gas exchange and water loss through permeable tube materials, as will be understood by those of skill in the art with reference to this disclosure.

In a most preferred embodiment, the tube is molded or made of a silicone based elastomer with a 0.03 inch inner diameter and 0.008 inch walls. This produces an expandable section having about a 0.2 inch inner diameter. A pressure of about 7 psi is sufficient to expand an annular tube made of a silicone elastomer.

Figure 2A:
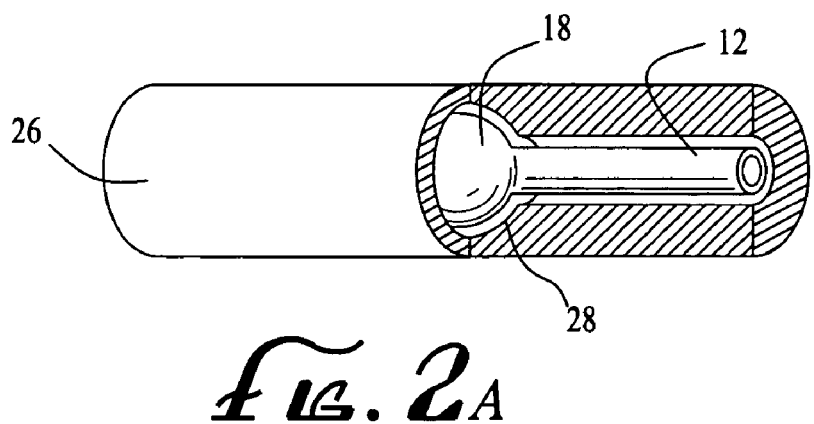
FIG. 2A is a front partial cut-away view of the annular tube in the second expanded shape, showing a first embodiment of a constraining sleeve.
Figure 2B:
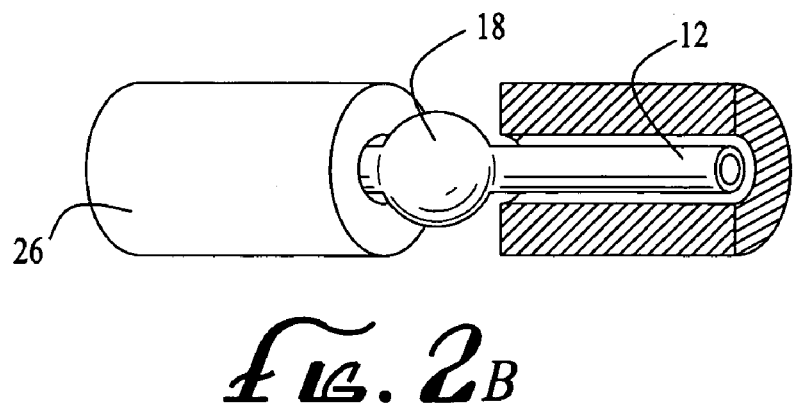
FIG. 2B is a front partial cut-away view of the annular tube in the second expanded shape, showing a second embodiment of a constraining sleeve.

Referring to FIGS. 2A and 2B, there is shown an alternate embodiment of the invention where the entire annular tube 12 is made of an elastomeric material, as described above, and a constraining sleeve 26 is used to control expansion of the annular tube 12. FIG. 2A, a front partial cut-away perspective view of the annular tube 12 in the second expanded shape 22, shows a first embodiment of the constraining sleeve 26. In this embodiment, the constraining sleeve 26 encompasses the entire length of the annular tube 12. A notch 28 in the constraining sleeve 26 allows the annular tube 12 to expand under pressure, the expandable section 18 of the annular tube 12 expanding to fill the notch 28. FIG. 2B, a front partial cut-away perspective view of the annular tube in the second expanded shape, shows a second embodiment of the constraining sleeve 26. In the embodiment shown in FIG. 2B, all but the expandable section 18 of the annular tube 12 is surrounded by a constraining sleeve 26. According to this embodiment, when the annular tube 12 is under pressure, the constraining sleeve 26 prevents expansion along the length of the annular tube 12, except for the expandable section 18 of the annular tube 12, which is unconstrained.

In an alternate embodiment, the expandable section 18 of the annular tube 12 is comprised of a thermally responsive material that is non-reactive with body fluids and reagents that may be acidic. Preferred materials are thermally responsive polymeric materials that have a preformed shape and can be elongated or deformed (i.e., expanded), and substantially recover from the deformation to the original preformed shape of the material in response to a change in temperature. Examples of such materials are known and can be utilized in the present invention, as will be understood by those of skill in the art with reference to this disclosure.

Figure 3:
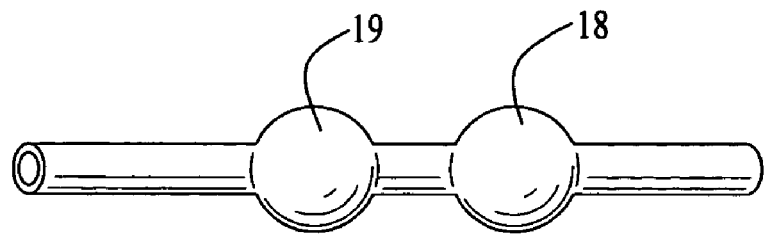
FIG. 3 is a front perspective view of an annular tube having multiple expandable sections along the length of the tube.

Referring now to FIG. 3, there is shown another embodiment of the invention, where the annular tube 12 has multiple expandable sections 18 and 19 along the length of the annular tube 12. The multiple expandable sections can be formed as described above by a combination of a change in the ambient physical environment of the annular tube 12 and an appropriate combination of dimensional and material properties of the annular tube 12.

Figure 4A:
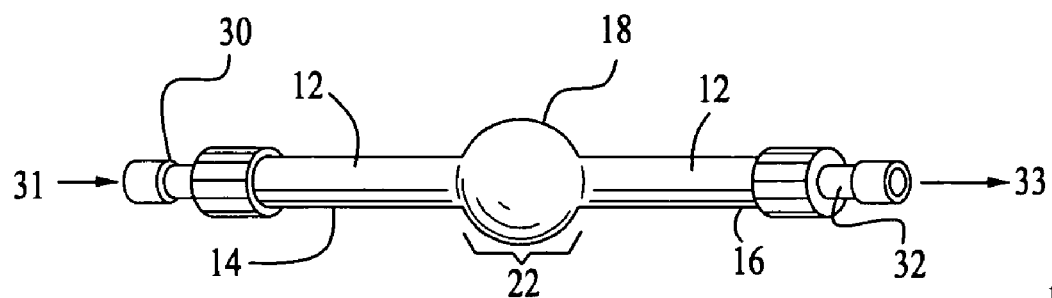
FIG. 4A is a front perspective view of a reaction vessel showing an annular tube having connectors according to another embodiment of the present invention.
Figure 4B:
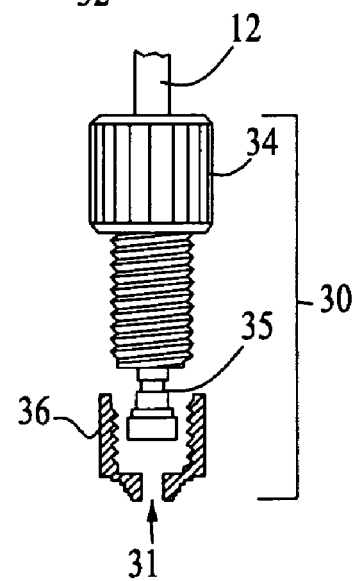
FIG. 4B is a front perspective view of a preferred threaded fitting connector.

Referring now to FIGS. 4A and 4B, there is shown another embodiment of the invention, where the annular tube 12, further comprises a first connector 30 for linking the annular tube inlet to a fluid source 31, and a second connector 32 for linking the annular tube outlet to a fluid receptacle 33. The first connector 30 and the second connector 32 can be the same or different and can be for example, a cemented connection, a barb-type fitting, a tapered syringe barrel, or a threaded fitting. FIG. 3B shows a preferred connector 30 and 32 comprising a threaded fitting having a nut 34, ferrule 35, and manifold 36. More preferably, the fitting is an Upchurch Scientific™ Fingertight™ fitting, available from Scivex™, Upchurch Scientific Division, having offices in Oak Harbor, Wash., US. As shown in FIG. 3B, an expanded view of the connector 30 shown in FIG. 3A, the fitting is a system having a nut 34 and a ferrule 35. The nut 34 has a central bore surrounded by an external (male) thread 36. The nut 34 engages the ferrule 35 and a manifold 36. The ferrule 35 has a collar with a conical exterior that mates with a conical counterbore concentric with the central bore of the nut 34. The manifold 36 has a flat bottom interior with a through bore comparable in size to the outer diameter of the annular tube 12. In use, the ferrule 35 and nut 34 slip over the end of the annular tube, and the nut 34 is screwed into the manifold. As the ferrule 35 bottoms out it mates with the counterbore and compresses the annular tube 12, holding the annular tube 12 in place. In certain embodiments, the annular tube may be too flexible for this configuration and the annular tube 12 can be supported in the region of the connection by a more rigid piece of inner supporting tube within the bore of the annular tube 12. This allows the nut 34 to compress the annular tube 12 between the ferrule 35 and the inner supporting tube. As will be understood by those of skill in the art with reference to this disclosure, other connectors and threaded fittings, such as the fittings described in Batts, John W., *All About Fittings*, 2003, available from Scivex™, Upchurch Scientific Division, Oak Harbor, Wash., US, can be used in the reaction vessel according to the present invention In a preferred, but not required embodiment, at least a portion of the interior of the annular tube 12 is coated. The internal walls of the annular tube 12 can be coated to prevent microparticles from attaching to the tube walls. Preferably, the tubes are transparent or translucent to enable the user to see the reaction or to perform a test, such as a colormetric test, or another test using a detection device, such as a laser, for in situ analysis. In an alternate embodiment, the annular tube is colored or labeled with a bar code.

According to another embodiment, the invention is an analytical system. Referring to FIG. 5, there is shown an illustration of a system having an annular tube, at least one expandable section 18 (shown in the second expanded shape 22), and a plurality of fluid sources 36, 38, and 40. The system has a first fluid source 36 for introducing a first fluid into the annular tube. The system can also have a second fluid source 38 for introducing a second fluid, which can be a wash liquid, into the annular tube, and a third fluid source 40 for introducing a third fluid into the annular tube. In a preferred, but not required embodiment, the third fluid contains a reactant to react with a component of the first fluid in the expandable section 18 of the annular tube 12 when the expandable section 18 is in the second expanded shape 22. When the expandable section 18 is in the second expanded shape 22, the expandable section 18 of the annular tube 12 acts as a reaction chamber for fluid samples introduced into the annular tube 12. Once fluids are introduced into the expandable section 18 and the annular tube 12 is in the second expanded shape 22, the mixing means 24 can be activated to combine the fluids. Alternately, the fluids can be pre-mixed before entering the tube. In a preferred, but not required embodiment, the inlet 14 is connected to a pump and the outlet 16 is closed. The outlet can be closed using a clamp or a valve. A preferred pump is a positive displacement pump with controllable dispense volumes to avoid overfilling tubes.

According to one embodiment of the present invention, the expandable section 18 is expanded by increasing the pressure inside the annular tube 12 by forcing fluid into the annular tube with a pump. The annular tube 12 can be emptied by aspirating the fluid from the annular tube 12 with a pump, thereby depressurizing the annular tube 12 and returning the annular tube 12 to the unexpanded first shape 20. Alternately, another channel at lower pressure can be connected to the annular tube 12 and used to expel the contents of the annular tube 12 into the channel. Once the annular tube 12 is empty, it can be flushed (i.e., washed) by coupling the inlet 14 to a pump (or another source of wash fluid) and the outlet 16 to a drain channel. Pushing wash fluid through the cross sectional area of the annular tube 12 displaces any expended reaction materials. Additional reactants can be added or an inert material can be forced in the annular tube 12 to displace the entire volume of the last reactant into the bubble.

In a more preferred, but not required embodiment, the system is used for detecting a detectable analyte in a fluid sample. According to this embodiment, the first fluid source 36 is a fluid sample having a detectable analyte. The second fluid source 38 is a detector fluid having a detector for the detectable analyte. The first fluid and the second fluid are introduced into the annular tube 12 at sufficiently high pressure such that the expandable section 18 of the annular tube 12 expands into the second expanded shape 22, thereby combining the first fluid and the second fluid in the expandable section 18. The third fluid source 40 is a wash liquid which is introduced into the annular tube 12 when the expandable section 18 of the annular tube 12 is substantially unexpanded. In a preferred, but not required embodiment, the first fluid is a fluid sample having a detectable analyte, such as a biological specimen from a patient, or other biological, chemical, and environmental specimens having a component to be analyzed or a detectable analyte.

In addition to a pump, the system can also have a controller, a pressure regulator, and/or various valves and filters for controlling the introduction of the fluid sources 36, 38, and 40 into the annular tube 18. In a variation of the present invention, the system can have an elongated bubble region that can serve as a pressurized reservoir to store and transfer relatively large fluid volumes without the need for a pump.

The system can also comprise one or more first connector 30 for linking one or more of the fluid source 36, 38, and 40 to the annular tube inlet 14, and one or more second connector 32 for linking the annular tube outlet to a fluid receptacle 33, or analytical devices such as a separation column, and/or an analyte detection system, including a detector and a data processor. In a preferred; but not required embodiment, the system has a detector for detecting the detectable analyte. According to one embodiment, samples can undergo a chemical or biochemical reaction prior to analysis and can be detected either in situ, such as through the wall of a transparent reaction vessel, or an aliquot of the reaction mixture can be removed by connecting a pump to one of the inlet 14 or the outlet 16 keeping the other end closed. The pump then aspirates part or all of the reaction vessel contents for further analysis.

Detectors and detection techniques that can be used in the system include spectrophotometry, fluorometry, radiometry, magnatometry, galvanometry, reflectrometry, ultrasonic detection, mephlometry, electrophoretic measurement, temperature measurement, pressure measurement, potentiometric measurement, amperometric measurement. A preferred detection technique uses a detectable chemical group, such as a fluorescent marker. However, other detectors and detection techniques are known and can be used according to the present invention, as will be understood by those of skill in the art with reference to this disclosure.

According to another embodiment of the present invention, a plurality of annular tubes can be used in parallel for multiple analyses. Referring now to FIG. 6, an illustration of a multiplex analysis system is shown. As illustrated in FIG. 6, the multiplex analysis system can have a plurality of fluid sources 42, 44, and 46 and a plurality of annular tubes 48 and 50. The multiplex system can be used for simultaneous or parallel reaction and/or detection of multiple reactions or multiple analytes. According to this embodiment, the system has multiple reaction chambers in a single device. The plurality of annular tube can be color or bar coded to correspond to different analytes being tested.

In another embodiment, the present invention is a method for an analytical reaction. In one embodiment, the method comprises selecting an annular tube having at least one expandable section, each expandable section having a first shape and a second expanded shape. Preferably, the volume of the second expanded shape is at least twice that of the first shape, and the portions of the annular tube adjoining the expandable section of the annular tube are substantially less expanded. A first fluid is then introduced into the annular tube, preferably by connecting an end of the annular tube to a pump, closing the other end of the annular tube, and forcing the first fluid into the expandable section of the annular tube with sufficient pressure to expand the expandable section to the second expanded shape.

Next, a second fluid is introduced into the annular tube. The second fluid can contain a reactant to react with a component of the first fluid in the expandable section of the annular tube when the expandable section of the annular tube is in the second expanded shape. The expandable section of the annular tube is then expanded into the second expanded shape, preferably by forcing the second fluid into the expandable section of the annular tube with a pump and further expanding the expandable section. The first and second fluids are then combined in the expanded section of the annular tube by mixing, such as by simple diffusion, or an active mixing method. Additional reactants can also be added to the annular tube and combined with the other fluids.

Next the contents of the annular tube can be analyzed in situ, or all or a portion of the combined first and second fluids in the annular tube are displaced from the expanded section of the annular tube. When the fluids are displaced from the expanded section of the annular tube, the expanded tube is returned to the original first shape. The contents of the annular tube can be aspirated, or an inert material can be forced into the annular tube to displace all or a portion of the volume of the reactants (i.e., the fluids) in the annular tube.

Once the reaction is complete, the reaction vessel is prepared for the next reaction by emptying the contents of the annular tube using a pump, or expelling the contents of the annular tube into another channel at lower pressure than that in the annular tube, taking advantage of the elastic energy stored in the expanded section of the annular tube. After the contents of the annular tube are expelled, a wash liquid is then introduced into the annular tube when the expandable section is in the first shape, preferably by coupling an end of the annular tube to a pump and pushing wash liquid through the annular tube thereby washing the annular tube.

In a preferred, but not required embodiment, the invention includes a method for detecting an analyte in a fluid sample. According to the present invention, an annular tube having at least one expandable section is selected. A fluid sample having a detectable analyte is then introduced into the annular tube, followed by introducing a detector fluid into the annular tube, the detector fluid containing a detector for the detectable analyte. The expandable section of the annular tube is then expanded into the second expanded shape at sufficiently high pressure such that the expandable section of the annular tube expands into the second expanded configuration thereby combining the fluid sample and the detector fluid in the expandable section. The contents of the annular tube can then be analyzed in situ for the detectable analyte and detector, or removed from the system and analyzed. The annular tube can then be washed and prepared for subsequent reuse.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts and drawings, and all the steps in any method or process disclosed, may be combined in any combination except combination where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

What is claimed is:

1. A system comprising:
   a) an annular tube having an inlet, an outlet, and at least one expandable section, each expandable section having a first shape and a second expanded shape, the volume of the second expanded shape being substantially expanded from that of the first shape, and the portions of the annular tube adjoining the expandable section of the annular tube being substantially less expanded and having substantially the same cross-sectional area as the first shape;
   b) a first fluid source for introducing a first fluid into the annular tube and reaction therein when the expandable section of the annular tube is in the second expanded shape; and
   c) a second fluid source for introducing second fluid into the annular tube when the expandable section of the annular tube is in the first shape, and further comprising a third fluid source for introducing a third fluid into the annular tube, the third fluid containing a reactant to react with a component of the first fluid in the expandable section when the annular tube is in the second expanded shape.

2. A system according to claim 1 wherein the component in the first fluid is an analyte and the reactant in the third fluid is a detector.

3. A system according to claim 2 wherein the detector is a detectable chemical group.

4. A system according to claim 1 further comprising one or more first connectors for linking one or more fluid sources to the annular tube inlet.

5. A system according to claim 1 further comprising one or more second connectors for linking the annular tube outlet to a fluid receptacle.

6. A system according to claim 1 further comprising a controller for controlling the introduction of one or more fluids into the annular tube.

7. A system according to claim 1 wherein the second fluid is a wash liquid, which is introduced into the annular tube for washing the annular tube.

8. A system according to claim 7 wherein the wash liquid is an inert fluid.

9. A system according to claim 1 further comprising means for introducing fluid into the annular tube.

10. A system according to claim 9 wherein the means for introducing fluid into the annular tube includes a pump.

11. A system comprising:
   a) an annular tube having an inlet, an outlet, and at least one expandable section, each expandable section having a first shape and a second expanded shape, the volume of the second expanded shape being substantially expanded from that of the first shape, and the portions of the annular tube adjoining the expandable section of the annular tube being substantially less expanded;
   b) a first fluid source for introducing a first fluid into the annular tube and reaction therein when the expandable section of the annular tube is in the second expanded shape; and
   c) a second fluid source for introducing second fluid into the annular tube when the expandable section of the annular tube is in the first shape, and further comprising means for mixing fluid in the expandable section.

12. A system according to claim 1 further comprising means for expanding the expandable section of the annular tube.

13. A system according to claim 12 wherein the means for expanding the expandable section of the annular tube includes closing a portion of the annular tube with a clamp or a valve.

14. A system according to claim 12 wherein the means for expanding the expandable section of the annular tube includes a constraining sleeve.

15. A system according to claim 12 wherein the expandable section comprises a thermally responsive material.

16. A system according to claim 12 wherein the means for expanding the expandable section of the annular tube includes means for varying pressure inside the annular tube.

17. A system for detecting an analyte in a fluid sample comprising:
   a) an annular tube having at least one expandable section, each expandable section having a first shape and a second expanded shape, the volume of the second expanded shape being at least twice that of the first shape, and the portions of the annular tube adjoining the expandable section of the annular tube being substantially less expanded and having substantially the same cross-sectional area as the first shape;
   b) a fluid sample source, the fluid sample having a detectable analyte;
   c) a detector fluid source, the detector fluid having a detector for the detectable analyte, the fluid sample and the detector fluid being introduced into the annular tube at sufficiently high pressure such that the expandable section of the annular tube expands into the second expanded shape thereby combining the fluid sample and the detector fluid in the expandable section;
   d) a wash liquid source for introducing wash liquid into the annular tube and washing the annular tube when the expandable section of the annular tube is at a sufficiently low pressure such that the expandable section is substantially unexpanded; and
   e) a controller for controlling the introduction of the sample fluid, detector fluid, and wash liquid into the inlet section.

18. A system according to claim 17 further comprising a pump for introducing fluids into the annular tube, wherein the pump is coupled to the annular tube.

19. The system of claim 1 wherein the diameter of the second expanded shape is greater than the diameters of the portions of the annular tube adjoining the expandable section of the annular tube.

20. The system of claim 1 wherein the first and third fluids are combined in the expandable section.

21. The system of claim 1 wherein the first fluid is in the first fluid source and the second fluid is in the second fluid source.

22. The system of claim 1 wherein the annular tube has only one lumen.

23. The system of claim 17 wherein the annular tube has only one lumen.

* * * * *

UNITED STATES PATENT AND TRADEMARK OFFICE
CERTIFICATE OF CORRECTION

PATENT NO. : 7,625,761 B2 Page 1 of 1
APPLICATION NO. : 10/903945
DATED : December 1, 2009
INVENTOR(S) : Michael L. Bell It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1441 days.

Signed and Sealed this

Second Day of November, 2010

David J. Kappos
*Director of the United States Patent and Trademark Office*